(12) United States Patent
Kawanaka

(10) Patent No.: US 6,876,985 B2
(45) Date of Patent: Apr. 5, 2005

(54) PATIENT INFORMATION MANAGEMENT METHOD AND SYSTEM EMPLOYING THE SAME

(75) Inventor: Tatsuo Kawanaka, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 411 days.

(21) Appl. No.: 10/147,409

(22) Filed: May 16, 2002

(65) Prior Publication Data

US 2003/0033258 A1 Feb. 13, 2003

(30) Foreign Application Priority Data

May 17, 2001 (JP) ........................................ 2001-148087

(51) Int. Cl.[7] ................................................. H04L 9/00
(52) U.S. Cl. ....................................... 705/51; 713/182
(58) Field of Search ............................... 705/3, 50, 51; 713/182, 201

(56) References Cited

U.S. PATENT DOCUMENTS

| | | |
|---|---|---|
| 3,727,190 A | 4/1973 | Vogelman et al. |
| 4,315,309 A | 2/1982 | Coli |
| 4,857,716 A | 8/1989 | Gombrich et al. |
| 5,265,010 A | 11/1993 | Evans-Paganelli et al. |
| 5,291,399 A | 3/1994 | Chaco |
| 5,301,105 A | 4/1994 | Cummings, Jr. |
| 5,361,202 A | 11/1994 | Doue |
| 5,410,704 A | 4/1995 | Norden-Paul et al. |
| 5,482,050 A | 1/1996 | Smokoff et al. |
| 5,546,580 A | 8/1996 | Seliger et al. |
| 5,592,945 A | 1/1997 | Fiedler |
| 5,666,476 A | 9/1997 | Kawanaka |
| 5,682,526 A | 10/1997 | Smokoff et al. |
| 5,713,350 A | 2/1998 | Yokota et al. |
| 6,131,090 A * | 10/2000 | Basso et al. .................... 705/3 |
| 6,148,342 A * | 11/2000 | Ho .............................. 713/201 |
| 6,182,220 B1 * | 1/2001 | Chen et al. .................. 713/182 |
| 2001/0051881 A1 * | 12/2001 | Filler ............................ 705/3 |
| 2002/0016923 A1 * | 2/2002 | Knaus et al. ................... 705/3 |
| 2002/0123909 A1 * | 9/2002 | Salisbury ....................... 705/3 |

FOREIGN PATENT DOCUMENTS

EP 869460 A2 * 10/1998 ............. G07F/7/10

OTHER PUBLICATIONS

"Keeping data safe:New HIPAA regs hit hard", Carrington, Telehealth Magazine, vol. 4, No. 6, p. 30(1), Oct. 1998.*
"The Dawn of HIPPA" Goedert, Health Data Management, vol. 8, No. 4, p. 84, Apr. 2000.*
"Someone to Watch over you.(personal electronic companion to manage your medical history)", Motluk, New Scientist, vol. 167, #22258, p. 28, Sep. 30, 2000.*
"Mediconsult.com Launches First Internet Service To Link Consumers to the World's Leading Medical Specialists", Business Wire, p. 11041184, Nov. 4, 1997.*
Public Law 104–91, (Aug. 21, 1996) pp. 1–19.*

* cited by examiner

Primary Examiner—Salvatore Cangialosi
(74) Attorney, Agent, or Firm—Carl B. Horton, Esq.; Armstrong Teasdale LLP

(57) ABSTRACT

A patient information management method having a configuration described below is provided that makes it possible to provide efficiently patient information to an appropriate partner while maintaining the secret thereof. In a storage management device, patient information is encrypted so that it can be decrypted when both patient ID information and a password decided by a patient are used. The encrypted patient information is stored in a storage device. The storage management device issues a use request to the storage device to receive encrypted patient information, and uses patient ID information and a password to decrypt it for use.

13 Claims, 13 Drawing Sheets

MEDICAL IMAGE CREATING DEVICE

STORAGE MANAGEMENT DEVICE

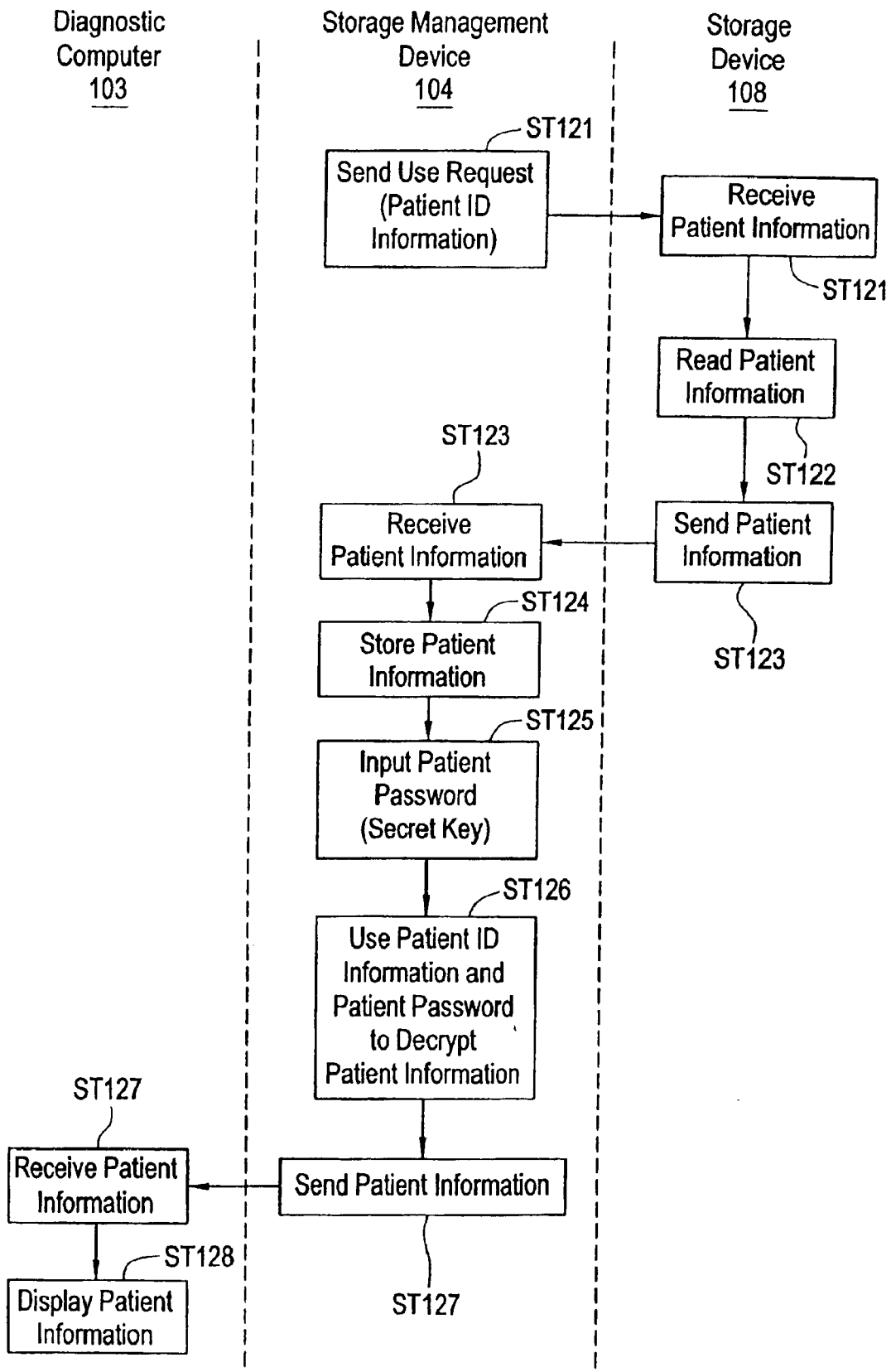

PATIENT INFORMATION MANAGEMENT METHOD AND SYSTEM EMPLOYING THE SAME

CROSS REFERENCE TO RELATED APPLICATIONS

This application claims the benefit of Japanese Application No. 2001-148087 filed May 17, 2001.

BACKGROUND OF THE INVENTION

The present invention relates to a patient information management method which enables a hospital or other organizations to store patient information in a public place while maintaining the secret thereof, and a system employing the method.

Patient information such as patient diagnostic information created by diagnostic devices and a doctor is useful for the doctor to know disease progress and previous treatments of a patient concerned when the patient comes to the hospital again for treatment. Therefore, the hospital stores the patient information in a storage device for a predetermined period. To store a huge amount of such patient information, the hospital must purchase and install a large-scale storage device having a large storage capacity.

However, there is a problem that the purchase and installation of a large-scale storage device imposes a large burden on the hospital spatially and economically. Also, since it is difficult to predict a storage capacity required for the storage device, there is a problem that, after the purchase of the storage device, the storage capacity of the storage device becomes insufficient or larger than needed.

In the case where a patient changes a current hospital, it is desirable that a new hospital can use patient information of the patient such as previous diagnostic information. However, conventionally, it has been difficult to efficiently use such patient information. Also, patient information should not be released without limitation because it relates to the privacy of a patient concerned and because of circumstances on the part of a hospital that created the patient information.

SUMMARY OF THE INVENTION

It is therefore an object of the present invention to provide a patient information management method that can relieve a hospital of the burden of storing patient information and to provide a system employing the method.

Also, it is another object of the present invention to provide a patient information management method that makes it possible to efficiently provide patient information to an appropriate partner according to the intention of a patient concerned and the hospital while maintaining the secret thereof and to provide a system employing the method.

To solve the above described problems of the prior art and achieve the above described objects, a patient information management method of a first invention is a method of managing patient information exchanged between an information use side that creates and uses the patient information, and an information storage side that stores the patient information, the method comprising the steps of: in the information use side, issuing patient identification information unique to the patient and encrypting patient information of the patient so that it can be decrypted when both the patient identification information and a password decided by the patient are used; sending the encrypted patient information from the information use side to the information storage side; in the information storage side, storing the encrypted patient information received from the information use side in a retrievable format; in response to a request from the information use side, sending the encrypted patient information pertaining to the request from the information storage side to the information use side; and in the information use side, using the encrypted patient information received from the information storage side after decrypting it by using the patient identification information and the password.

In the patient information management method of the first invention, preferably, the information use side and the information storage side associate and manage the patient identification information of the patient and the patient information. Also, in the patient information management method of the first invention, preferably, the information use side sends the request to the information storage side together with the patient identification information, and the information storage side reads the encrypted patient information corresponding to the patient identification information received from the information use side, and sends the read encrypted patient information to the information use side. In the patient information management method of the first invention, preferably, the information storage side charges the information use side when the encrypted patient information is sent to the information use side. In the patient information management method of the first invention, preferably, the information use side stores the patient information for a first period, and the information storage side stores the encrypted patient information for a second period longer than the first period.

A patient information management method of a second invention is a method of managing patient information exchanged among a first information use side that creates and uses the patient information, an information storage side that stores the patient information, and a second information use side that uses the patient information, the method comprising the steps of: in the first information use side, issuing patient identification information unique to the patient and encrypting patient information of the patient so that it can be decrypted when both the patient identification information and a password decided by the patient are used; sending the patient identification information and the encrypted patient information from the first information use side to the information storage side; in the information storage side, associating and storing the patient information and the encrypted patient information received from the first information use side; in the second information use side, specifying the patient identification information to issue a request to use the patient information to the information storage side; in the information storage side, in response to the request, sending the encrypted patient information corresponding to the patient identification information specified in the request to the second information use side; and in the second information use side, using the encrypted patient information received from the information storage side after decrypting it by using the patient identification information and the password.

In the patient information management method of the second invention, preferably, the patient obtains the patient identification information from the first information use side and provides the patient identification information to the second information use side.

A patient information management system of a third invention has a storage management device provided in an information use side using patient information and a storage device provided in an information storage side storing the patient information, wherein the storage management device comprises: an issuing means for issuing patient identification information unique to the patient; an encrypting means for encrypting patient information of the patient so that it can be decrypted when both the patient identification information and a password decided by the patient are used; a first sending means for sending the encrypted patient information and a request to use the patient information to the storage device; a first receiving means for receiving the encrypted patient information from the storage device; and a decrypting means for decrypting the received encrypted patient information by using the patient identification information and the password; and the storage device comprises: a second receiving means for receiving the encrypted patient information and the request from the storage management device; a storing means for storing the received encrypted patient information; a control means for reading the encrypted patient information from the storing means in response to the request; and a second sending means for sending the read encrypted patient information to the storage management device.

Hereinafter, the operation of the patient information management system of the third invention is described. Patient information of a patient is encrypted by the encrypting means of the storage management device so that it can be decrypted when both patient identification information and a password decided by the patient are used. The encrypted patient information and a request to use the patient information are sent from the sending means to the storage device and are received by the second receiving means of the storage device. The encrypted patient information received by the second receiving means is stored in the storing means of the storage device. When the second receiving means receives a request to use the patient information from the storage management device, the encrypted patient information is read from the storing means by the control means. The read encrypted patient information is sent from the second sending means of the storage device to the storage management device. The encrypted patient information is received by the first receiving means of the storage management device and is decrypted using the patient identification information and the password in the decrypting means.

In the patient information management system of the third invention, preferably, the storage management device and the storage device associate and manage the patient identification information of the patient and the patient information. In the patient information management system of the third invention, preferably, the first sending means of the storage management device sends the request to the storage device together with the patient identification information, the second receiving means of the storage device receives the patient identification information, the control means of the storage device reads the encrypted patient information corresponding to the patient identification information received by the second receiving means from the storing means, and the second sending means of the storage device sends the read encrypted patient information to the storage management device.

In the patient information management system of the third invention, preferably, the storage device charges the information use side when the patient information is sent to the information use side.

A patient information management system of a fourth invention has a first storage management device provided in a first information use side using patient information, a storage device provided in an information storage side storing the patient information, and a second storage management device provided in a second information use side using the patient information, wherein the first storage management device comprises: an issuing means for issuing patient identification information unique to the patient; an encrypting means for encrypting patient information of the patient so that it can be decrypted when both the patient identification information and a password decided by the patient are used; and a first sending means for sending the encrypted patient information to the storage device together with the patient identification information; the second storage management device comprises: a sending means for specifying the patient identification information to send a request to use the patient information; a first receiving means for receiving the encrypted patient information from the storage device; and a decrypting means for decrypting encrypted patient information received by the first receiving means; and the storage device comprises: a second receiving means for receiving the encrypted patient information from the first storage management device and receiving the use request from the second storage management device; a storing means for storing the received encrypted patient information; a control means for reading the encrypted patient information from the storing means in response to the use request; and a second sending means for sending the read encrypted patient information to the second storage management device. In this case, the storage device charges the second storage management device, for example, when the patient information is sent to the second storage management device.

Therefore, the present invention can provide a patient information management method that can relieve a hospital of the burden of storing patient information, and a system employing the method. Also, the present invention can provide a patient information management method that makes it possible to efficiently provide patient information to an appropriate partner according to the intention of a patient concerned and the hospital while maintaining the secret thereof, and a system employing the method.

Further objects and advantages of the present invention will be apparent from the following description of the preferred embodiments of the invention as illustrated in the accompanying drawings.

BRIEF DESCRIPTION OF THE DRAWINGS

FIG. 13 is a flowchart for explaining an operation of the medical system in the case where the hospital 110 uses patient information stored in a storage device by the hospital 10.

DETAILED DESCRIPTION OF THE PRESENT INVENTION

Hereinafter, a medical system according to preferred embodiments of the present invention is described.

First Embodiment

Figure 1:
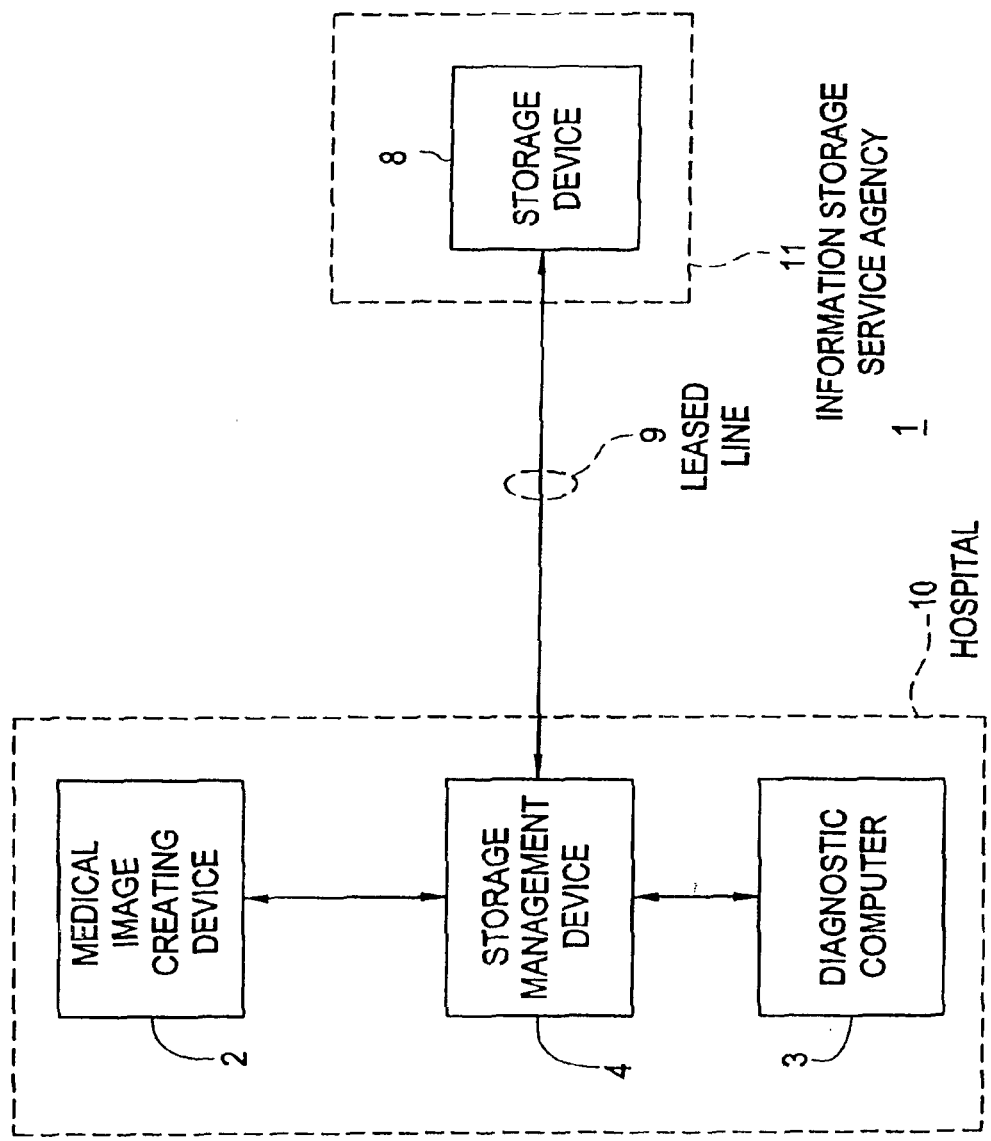
FIG. 1 is an overall configuration diagram of a medial system according to a first embodiment of the present invention.

FIG. 1 is an overall configuration diagram of a medial system 1 according to an embodiment of the present invention. As shown in FIG. 1, the medical system 1 comprises a medical image creating device 2, a diagnostic computer 3, a storage management device 4, and a storage device 8. The medical image creating device 2, diagnostic computer 3, and storage management device 4 are disposed in a hospital and is used by, e.g., employees of the hospital 10. The storage device 8, used by an information storage service agency 11, is connected to the storage management device 4 over a leased line 9. The hospital 10 makes a contract with the information storage service agency 11 to commit storage of patient information.

The present embodiment corresponds to first and third inventions. An information use side of the present invention corresponds to the hospital 10 and an information storage side corresponds to the information storage service agency 11.

Hereinafter, components shown in FIG. 1 are described in detail.

[Medical Image Creating Device 2]

Figure 2:
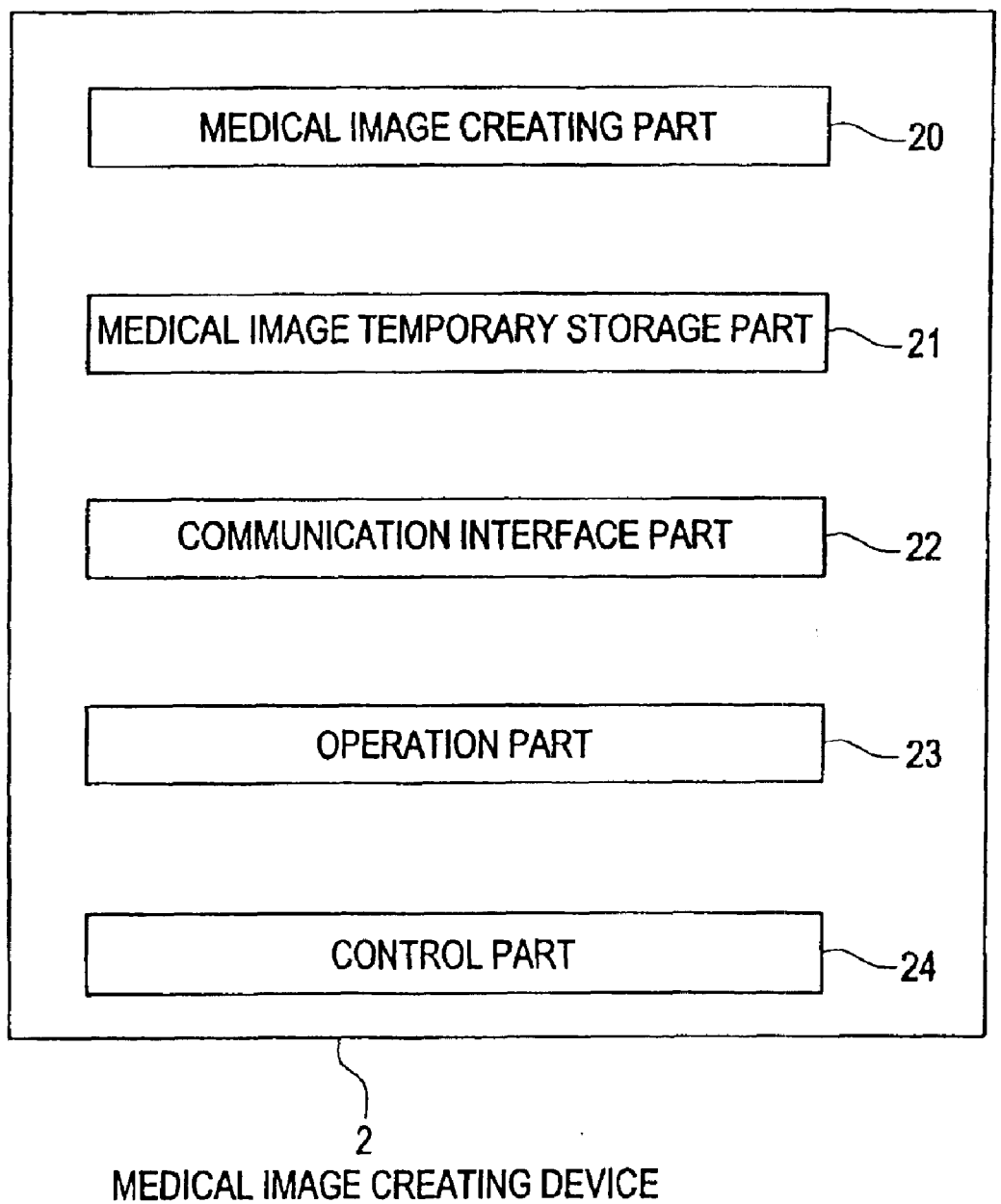
FIG. 2 is a functional block diagram of a medical image creating device 2 shown in FIG. 1.

FIG. 2 is a functional block diagram of the medical image creating device 2 shown in FIG. 1. As shown in FIG. 2, the medical image creating device 2 has a medical image creating part 20, a medical image temporary storage part 21, a communication interface part 22, an operation part 23, and a control part 24. The medical image creating device 2 is, for example, an X-ray CT (Computed Tomography) device, MRI (Magnetic Resonance Imaging) device, CR (Computed Radiography) device, and DR (Digital Radiography) device.

When the medical image creating device 2 is X-ray CT device, MRI device, CR device, or DR device, the medical image creating part 20 performs imaging processing corresponding to them to create image data used as medical image information.

The medical image temporary storage part 21 temporarily stores medical image information created by the medical image creating part 20.

The communication interface part 22 is an interface for performing communications with the storage management device 4.

The operation part 23 is an operation means such as a keyboard and a mouse, and outputs operation signals corresponding to operations by an operator to the control part 24.

The control part 24 controls the operation of the medical image creating device 2.

[Diagnostic Computer 3]

Figure 3:
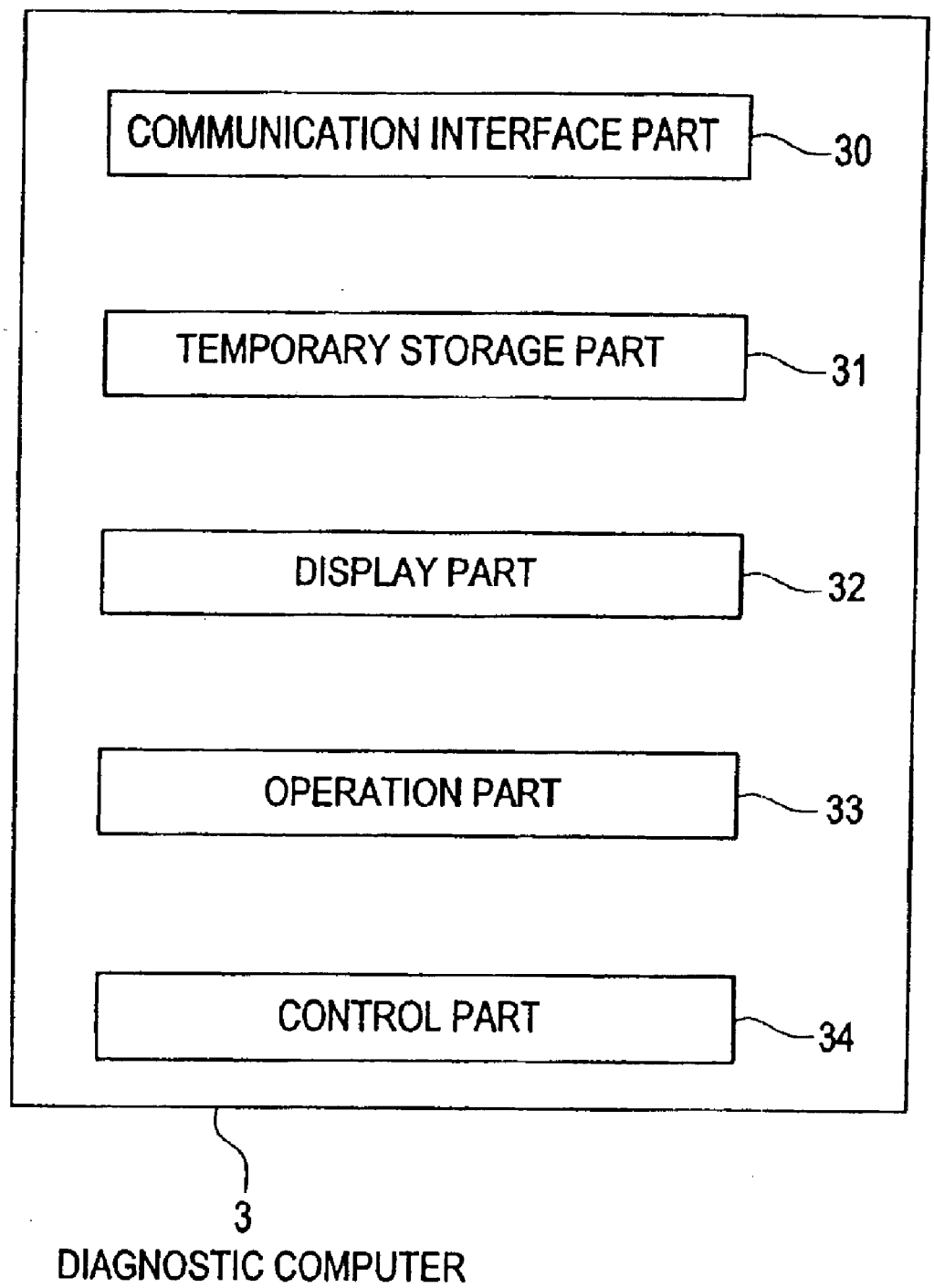
FIG. 3 is a functional block diagram of a diagnostic computer shown in FIG. 1.

FIG. 3 is a functional block diagram of a diagnostic computer 3 shown in FIG. 1. As shown in FIG. 3, the diagnostic computer 3 has a communication interface part 30, a temporary storage part 31, a display part 32, an operation part 33, and a control part 34.

The communication interface part 30 is an interface for performing communications with the storage management device 4.

The temporary storage part 31 temporarily stores patient information inputted through the communication interface part 30 and diagnostic information inputted from the operation part 33.

The display part 32, for example, displays an image corresponding to patient information read from the temporary storage part 31.

The operation part 33 is an operation means such as a keyboard and a mouse, and outputs operation signals corresponding to operations by an operator to the control part 34.

The control part 34 controls the operation of the medical image creating device 3 in a centralized manner.

[Storage Management Device 4]

Figure 4:
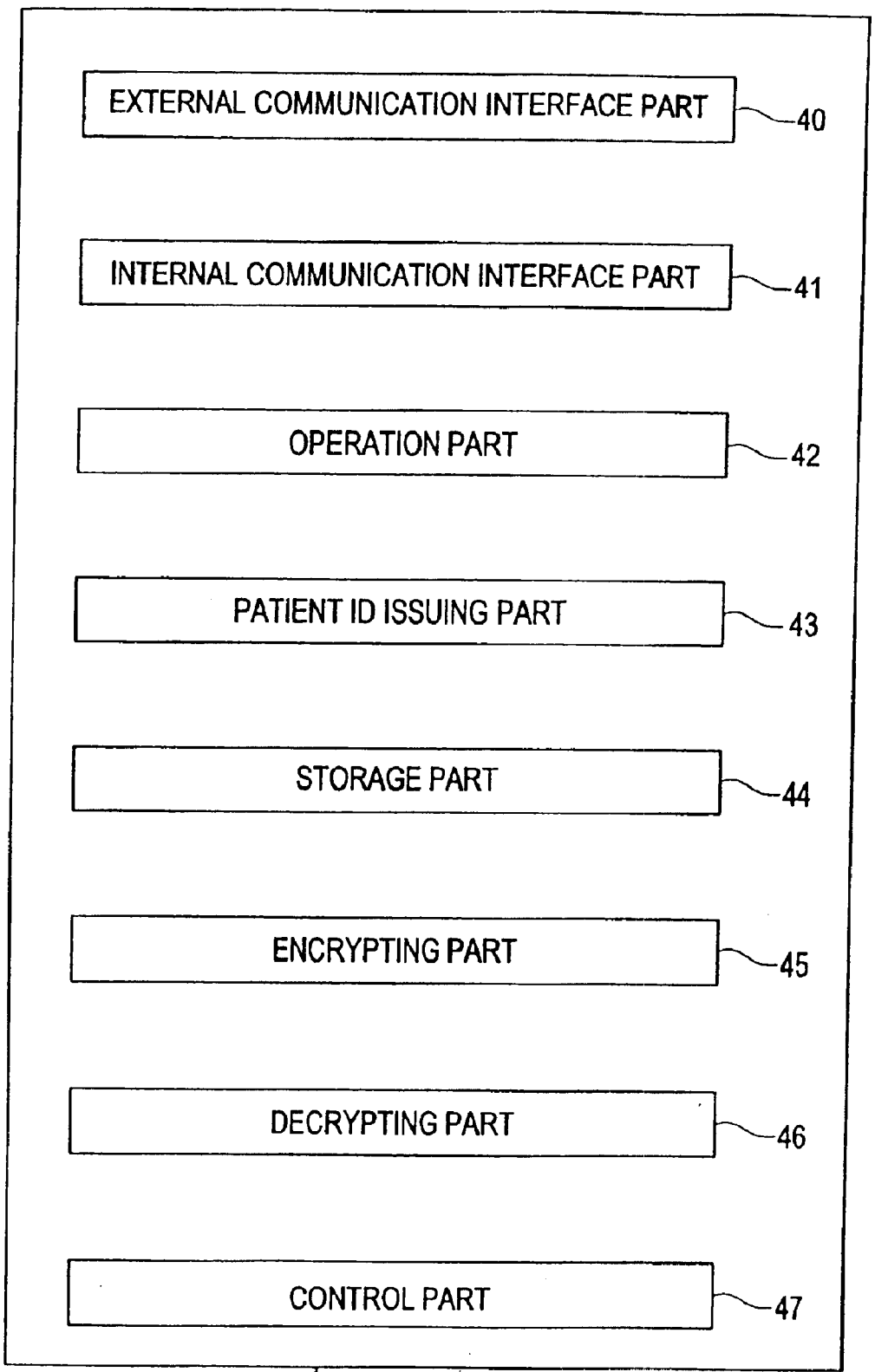
FIG. 4 is a functional block diagram of a storage management device shown in FIG. 1.

FIG. 4 is a functional block diagram of the storage management device 4 shown in FIG. 1. As shown in FIG. 4, the storage management device 4 has an external communication interface part 40, an internal communication interface part 41, an operation part 42, a patient ID issuing part 43, a storage part 44, an encrypting part 45, a decrypting part 46, and a control part 47. The external communication interface part 40 corresponds to a first sending means and a first receiving means of a third invention, the patient ID issuing part 43 corresponds to an issuing means of the third invention, the encrypting part 45 corresponds to an encrypting means of the third invention, and the decrypting part 46 corresponds to a decrypting part of the third invention.

The external communication interface part 40 performs communications with the storage device 8 over the leased line 9.

The internal communication interface part 41 performs communications with the medical image creating device 2 and the diagnostic computer 3.

The operation part 42 is an operation means such as a keyboard and a mouse, and creates operation signals corresponding to operations by an operator or patient. The operation part 42 is used, for example, by an operator to input patient ID information, or a patient to input a password.

The patient ID issuing part 43 issues patient ID information (patient identification information of the present invention) unique to a patient.

The storage part 44 stores patient information such as patient ID information, patient personal information, and diagnostic information. The storage part 44, for examples, stores patient information for one year and deletes it after one year elapses. The encrypting part 45, when sending patient information to the storage device 8, encrypts the patient information by using patient ID information and a password of a pertinent patient so that it is decrypted only when both the patient ID information and the password are used.

The decrypting part 46 decrypts encrypted patient information received from the storage device 8 by using both patient ID information and password of a pertinent patient.

The control part 47 controls processing of the storage management device 4 in a centralized manner.

[Storage Device 8]

Figure 5:
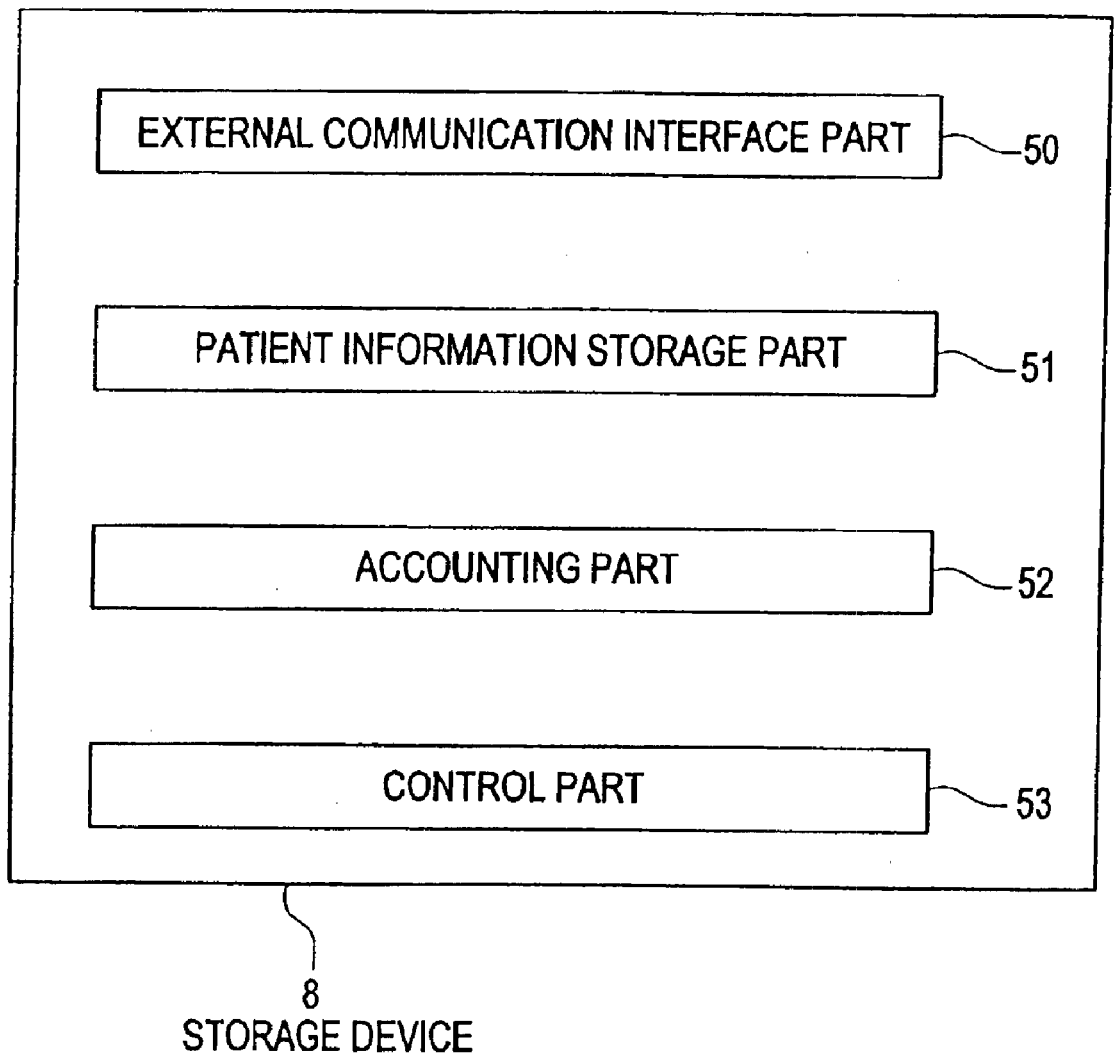
FIG. 5 is a functional block diagram of a storage device shown in FIG. 1.

FIG. 5 is a functional block diagram of the storage device 8 shown in FIG. 1. As shown in FIG. 5, the storage device 8 has an external communication interface part 50, a patient information storage part 51, an accounting part 52, and a control part 53. The external communication interface part 50 corresponds to a second receiving means and a second sending means of the third invention, the patient information storage part 51 corresponds to a storing means of the third invention, the accounting part 52 corresponds to an accounting means of the third invention, and the control part 53 corresponds to a control part of the third invention.

The external communication interface part 50 performs communications with the storage device 4 over the leased line 9.

The patient information storage part 51 is a so-called image library that stores encrypted patient information received from the storage management device 4 through the external communication interface part 50 in a retrievable format. The patient information storage part 51, for example, stores patient information for 10 years in accordance with contract with the hospital 10. As the patient information storage part 51, e.g., HDD is used.

The accounting part 52 charges the hospital 10 for transmission of patient information to the storage management device 4. At this time, the accounting part decides amounts to be charged according to the amount of patient information sent to the storage management device 4.

The control part 53 controls the operation of the storage device 8 in a centralized manner.

First Operation Example

Hereinafter, an operation of the medical system 1 is described.

[First Embodiment]

Figure 6:
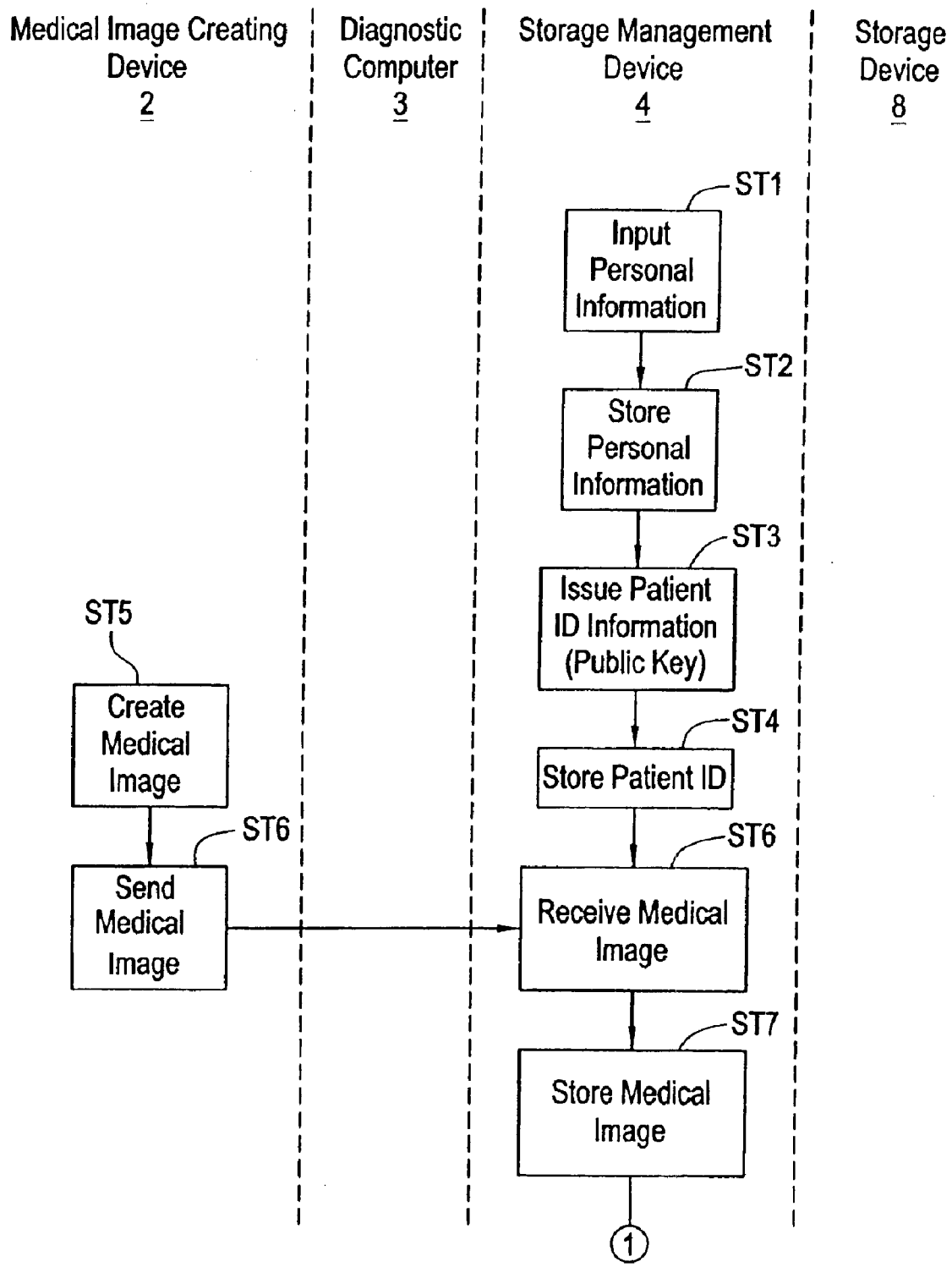
FIG. 6 is a flowchart for explaining an operation of the medical system shown in FIG. 1, from creation of medical image information and diagnostic information to storage of patient information in a storage device.
Figure 7:
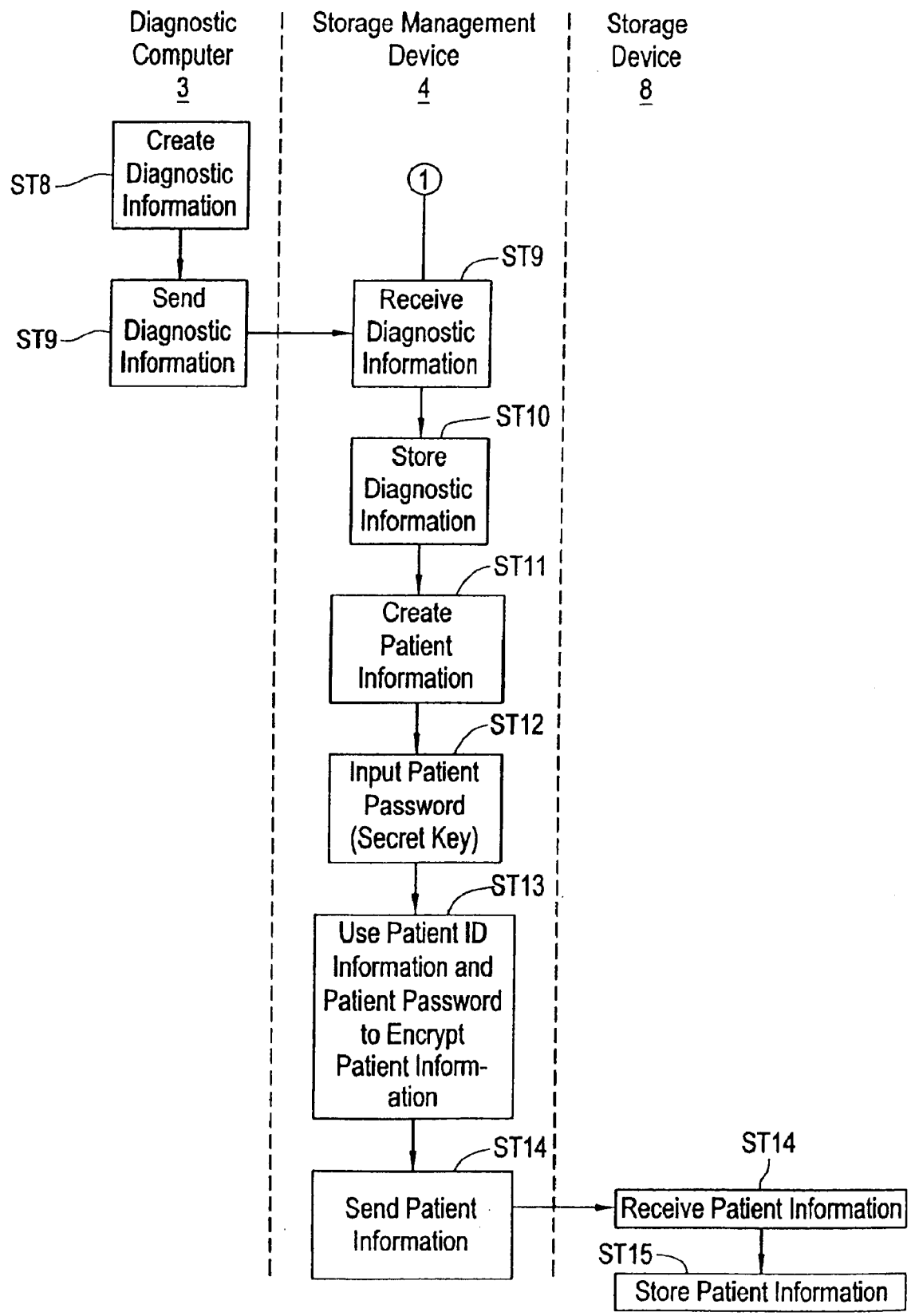
FIG. 7 is a flowchart for explaining an operation of the medical system shown in FIG. 1, from creation of medical image information and diagnostic information to storage of patient information in the storage device.

Hereinafter, a description is made of an operation of the medical system 1, from creation of medical image information and diagnostic information to storage of patient information in the storage device 8. FIGS. 6 and 7 are flowcharts for explaining the operation example.

Step ST1:

An operator operates the operation part 42 of the storage management device 4 shown in FIG 4 to input a patient name, sex, birthday, and other personal information.

Step ST2:

The personal information inputted in step ST1 is stored in the storage part 44 shown in FIG. 4.

Step ST3:

Patient ID information (public key) specific to the patient is created by the patient ID issuing part 43 shown in FIG. 4.

Step ST4:

The patient ID information created in step ST3 is stored in the storage part 44 shown in FIG. 4 after being associated with the personal information stored in step ST2.

Step ST5:

The operator operates the operation part 23 shown in FIG. 2 to create a medical image information of the patient in the medical image creating part 20. The medical image information is temporarily stored in the medical image temporary storage part 21.

Step ST6:

The medical image information stored in the medical image temporary storage part 21 in step ST5 is sent to the storage management device 4 through the communication interface part 22 shown in FIG. 2. The medical image information is received in the internal communication interface part 41 of the storage management device 4 shown in FIG. 4.

Step ST7:

The medical image information received in step ST6 is stored in the storage part 44 of the storage management device 4 shown in FIG. 4.

Step ST8:

Diagnostic information of the patient is created when a doctor operates the operation part 33 of the diagnostic computer 3 shown in FIG. 3.

Step ST9:

The diagnostic information created in step ST8 is sent to the storage management device 4 through the communication interface part 30 of the diagnostic computer 3 shown in FIG. 3. The diagnostic information is received in the internal communication interface part 41 of the storage management device 4 shown in FIG. 4.

Step ST10:

The diagnostic information received in step ST9 is stored in the storage part 44 of the storage management device 4 shown in FIG. 4.

Step ST11:

By the control part 47 shown in FIG. 4, patient information is created which consists of the personal information stored in step ST2, the patient ID information stored in step ST4, the medical image information stored in step ST7, and the diagnostic information stored in step ST10.

Step ST12:

By the patient operating the operation part 42 of the storage management device 4 shown in FIG. 4, a password (secret key) decided by the patient and known only by the patient is inputted.

Step ST13:

By the encrypting part 45 of the storage management device 4 shown in FIG. 4, using the patient ID information of the patient read from the storage part 44 and the patient password inputted in the step ST12, the patient information created in step ST11 is encrypted so that it can be decrypted only when the patient ID information and the patient password are used.

Step ST14:

The patient ID information of the patient and the patient information encrypted in step ST13 are sent to the storage device 8 over the leased line 9 from the external communication interface part 40 of the storage management device 4 shown in FIG. 4. The patient ID information and the encrypted patient information are received in the external communication interface part 50 of the storage device 8 shown in FIG. 5.

Step ST15:

The patient ID information and the encrypted patient information that were received in step ST14 are associated with each other and stored in the patient information storage part 51 of the storage device 8 shown in FIG. 5.

Second Operation Example

Figure 8:
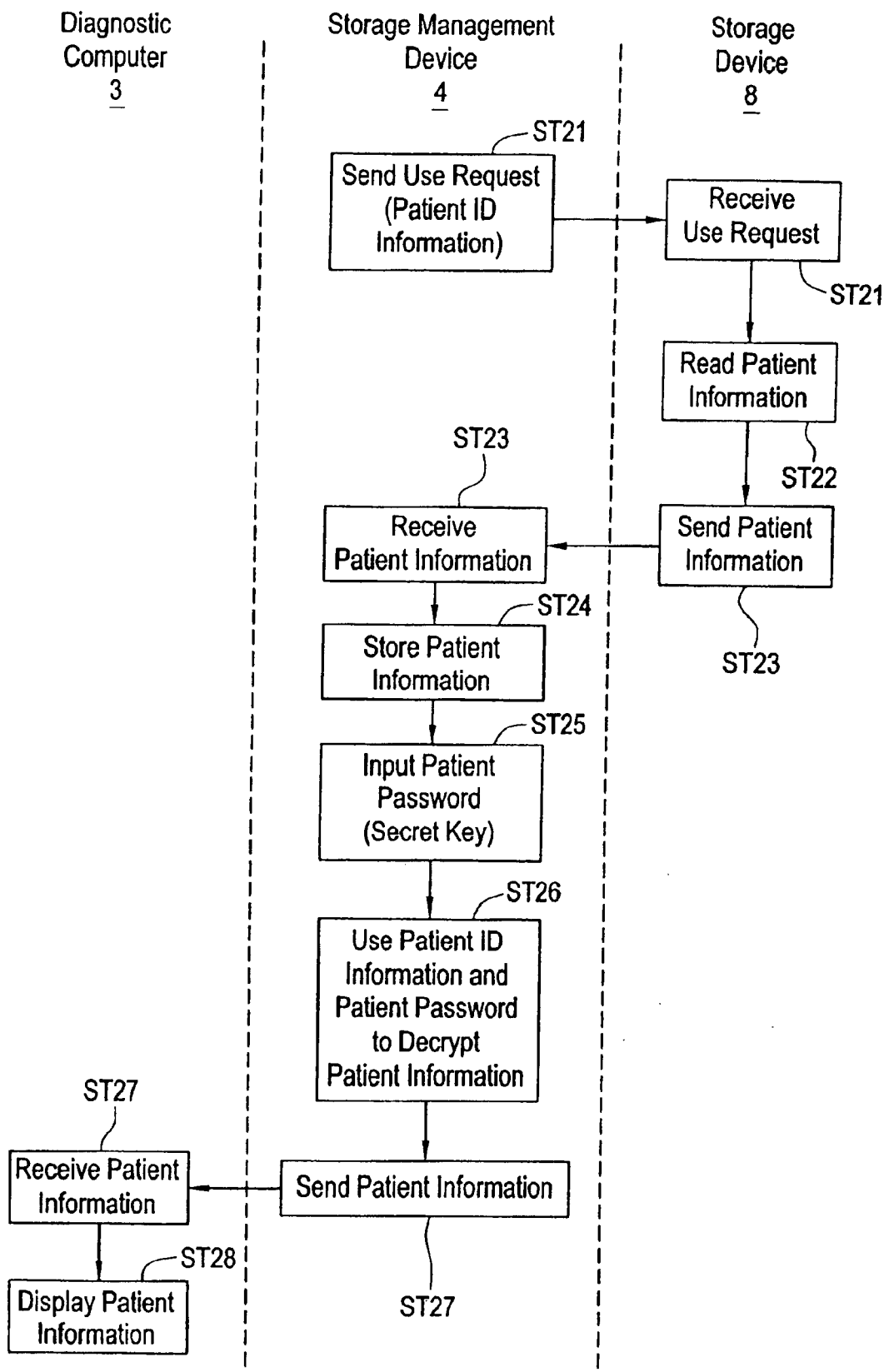
FIG. 8 is a flowchart for explaining an operation of the medical system in the case where patient information stored in the storage device by processing of FIGS. 6 and 7 is used in a hospital.

Hereinafter, a description is made of an operation of the medical system in the case where the patient information stored in the storage device 8 by execution of the above described first operation example is used in the hospital 10. FIG. 8 is a flowchart for explaining the operation example.

Step ST21:

The operation part 42 of the storage management device 4 shown in FIG. 4 is operated by the operator, patient ID information of a patient whose patient information is to be obtained from the storage device 8 is inputted, and a patient information use request specifying the patient ID information is created by the control part 47. The patient information use request is sent to the storage device 8 through the external communication interface part 40 shown in FIG. 4. The patient information use request is received in the external communication interface part 50 of the storage device 8 shown in FIG. 5.

Step ST22:

By the control part 53 shown in FIG. 5, encrypted patient information is read from the patient information storage part 51 by using the patient ID information specified in the patient information use request received in step ST21 as key.

Step ST23:

The encrypted patient information read in step ST22 is sent to the storage management device 4 over the leased line 9 from the external communication interface part 50 of the storage device 8 shown in FIG. 5. The encrypted patient information is received in the external communication interface part 40 of the storage management device 4 shown in FIG. 4.

Step ST24:

The encrypted patient information received in step ST23 is stored in the storage part 44 of the storage management part 4 shown in FIG. 4.

Step ST25:

A patient operates the operation part 42 of the storage management device 4 shown in FIG. 4 to input a patient password (secret key).

Step ST26:

By the decrypting part 46 of the storage management device 4 shown in FIG. 4, the encrypted patient information stored in step ST24 is decrypted using the patient ID information read from the storage part 44 and the patient password inputted in step ST25.

Step ST27:

The patient information decrypted in step ST26 is sent from the internal communication interface part 41 of the storage management device 4 shown in FIG. 4 to the diagnostic computer 3. The patient information is received in the communication interface part 30 of the diagnostic computer 3 shown in FIG. 3.

Step ST28:

The display part 32 of the diagnostic computer 3 shown in FIG. 3 displays an image reflecting the patient information received in step ST27.

As has been described above, according to the medical system 1, the hospital 10 does not need to purchase and install a large-size and expensive storage device to have the information storage service agency 11 store patient information. Also, according to the medical system 1, since patient information sent from the storage management device 4 to the storage device 8 is encrypted so that it is decrypted only when both patient ID information and password are used, the information storage service agency 11 cannot know the contents of the patient information and a patient corresponding to the patient information. Consequently, the secret of the patient information is maintained.

According to the medical system 1, since patient information created by the hospital 10 is stored in the information storage service agency 11, which is an organization independent from the hospital 10, the hospital 10 can prove that the patient information is not tampered, from update history information of patient information stored in the storage device 8.

Second Embodiment

Figure 9:
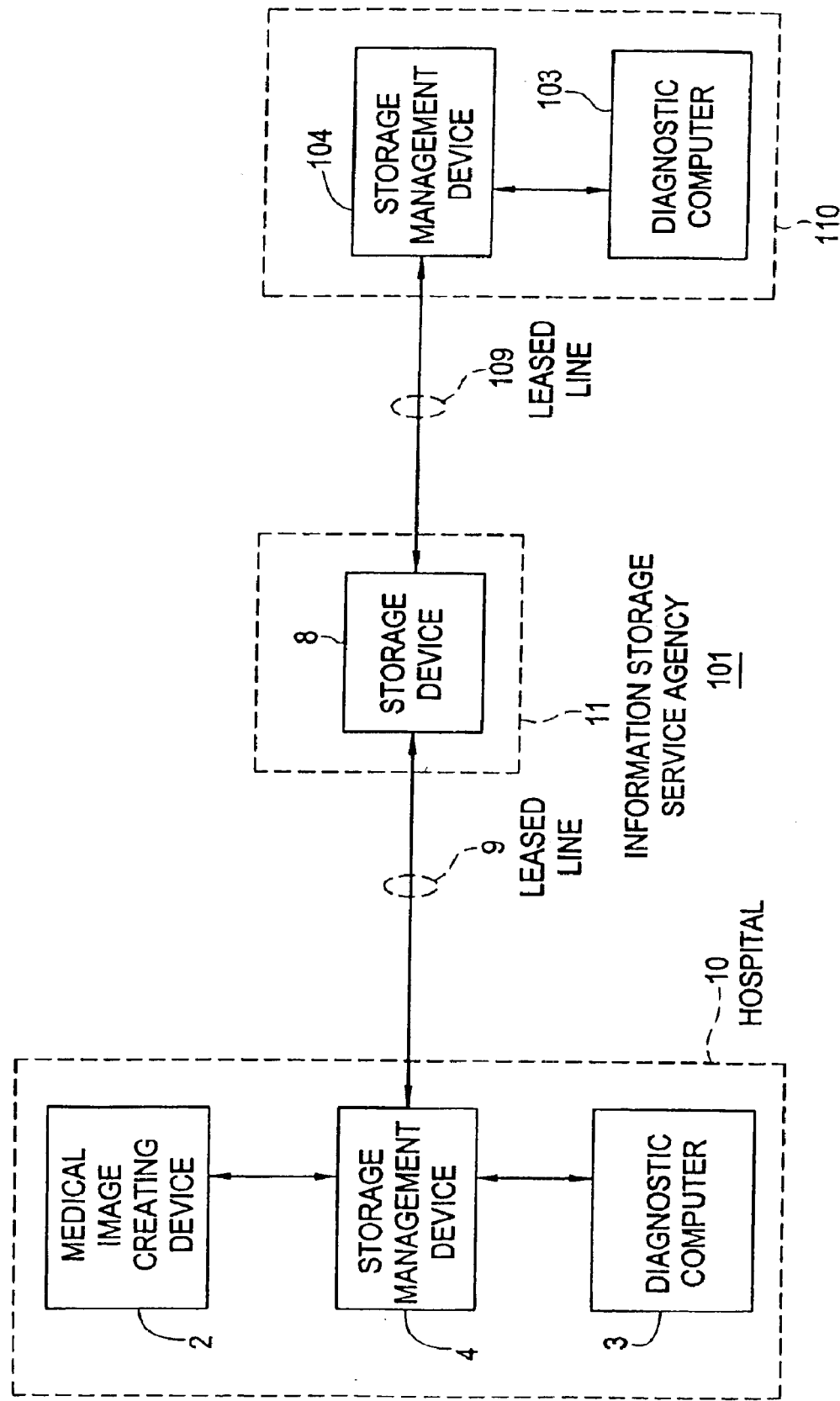
FIG. 9 is an overall configuration diagram of a medical system according to a second embodiment of the present invention.

FIG. 9 is an overall configuration diagram of a medical system 101 according to a preferred embodiment of the present invention. As shown in FIG. 9, the medical system 101 has a medical image creating device 2, a diagnostic computer 3, a storage management device 4, a storage device 8, a diagnostic computer 103, and a storage management device 104. The medical image creating device 2, diagnostic computer 3, and storage management device 4 are disposed within a hospital 10 and are used by, e.g., employees of the hospital 10. The storage device 8, used by the information storage service agency 11, is connected to the storage management device 4 over the leased line 9 and is connected to the storage management device 104 over a leased line 109.

The diagnostic computer 103 and the storage management device 104 are disposed within a hospital 110 and is used by employees of the hospital 110. In FIG. 9, the medical image creating device 2, the diagnostic computer 3, the storage management device 4, the storage device 8, the leased line 9, and the hospital 10 that have the same reference numerals as those in FIG. 1 are the same as those having the same reference numerals described in the first embodiment. The storage device 8 has the function of performing communications with the storage management device 104 over the leased line 109, in addition to the function described in the first embodiment.

The present embodiment is an embodiment corresponding to second and fourth inventions. The storage management device 4 corresponds to a first storage management device of the fourth invention, the storage device 8 corresponds to a storage device of the fourth invention, and the storage management device 104 corresponds to a second storage management device of the fourth invention. The hospital corresponds to a first information use side of the second invention, the information storage service agency 11 corresponds to an information storage side of the second invention, and the hospital 110 corresponds to a second information use side of the second invention.

The hospitals 10 and 110 make a contract with the information storage service agency 11 on storage and use of patient information.

Figure 10:
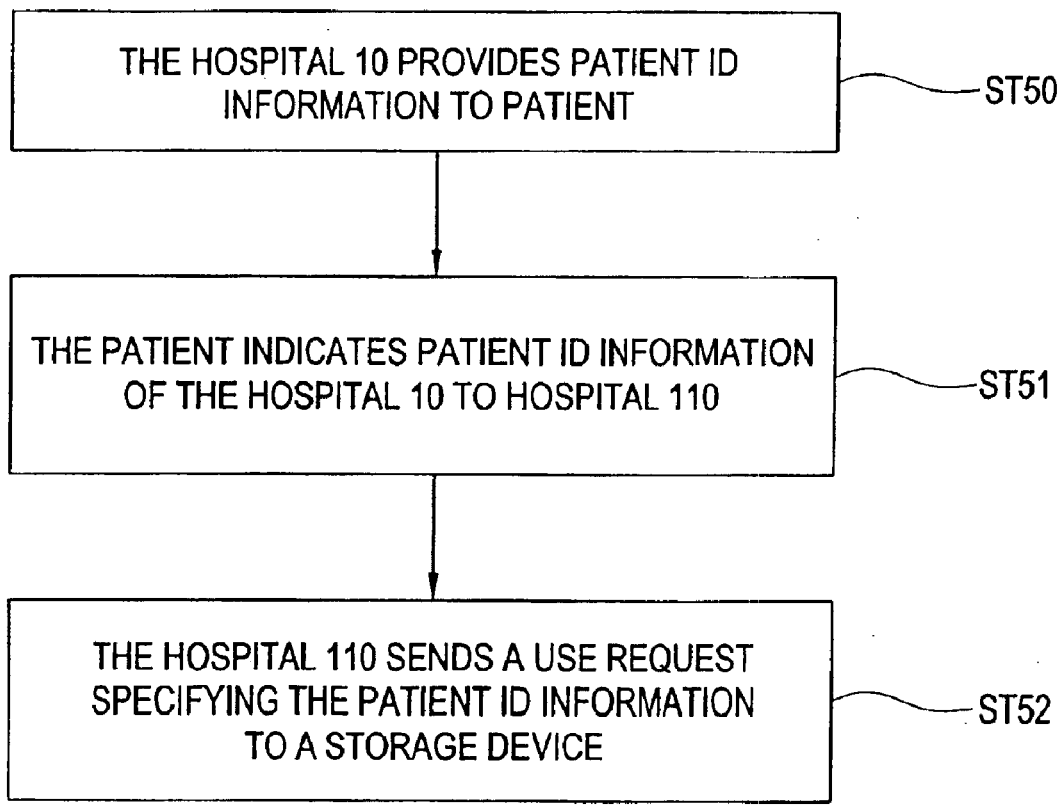
FIG. 10 is a diagram for explaining a procedure to be performed by a patient having been examined in the hospital 10 in the case where he (she) is to receive examination in a hospital 110.

In the medical system 101, as shown in FIG. 10, in the case where a patient having been examined in the hospital 10 is to receive examination in the hospital 110, the hospital 110 can use patient information of the patient committed to the information storage service agency 11 for storage by the hospital 10. In this case, as shown in FIG. 10, in response to a request from the patient, the hospital 10 provides patient ID information to the patient (step ST50 ), and the patient passes the patient ID information to the hospital 110 (step ST51 ). The hospital 110 uses the patient ID information of the patient to issue a patient information use request to the storage device 8 (step ST52 ).

Hereinafter, a description will be made of the configuration of the diagnostic computer 103 and the storage management device 104 shown in FIG. 9.

[Diagnostic Computer 103]

Figure 11:
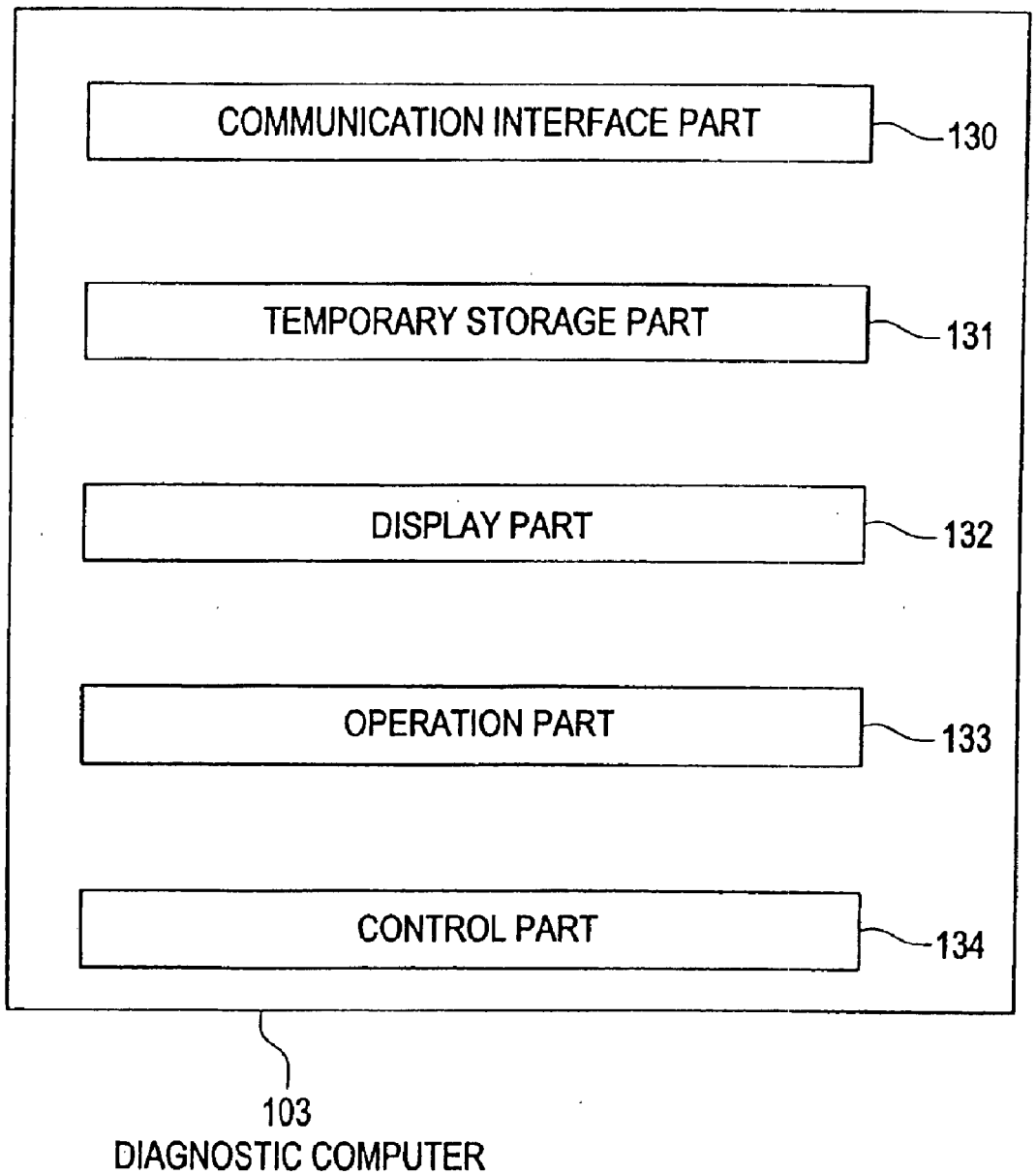
FIG. 11 is a functional block diagram of the diagnostic computer 103 shown in FIG. 9.

FIG. 11 is a functional block diagram of the diagnostic computer 103 shown in FIG. 9. As shown in FIG. 11, the diagnostic computer 103 has a communication interface part 130, a temporary storage part 131, a display part 132, an operation part 133, and a control part 134. The communication interface part 130, the temporary storage part 131, the display part 132, the operation part 133, and the control part 134 are respectively basically the same as the communication interface part 130, the temporary storage part 131, the display part 132, the operation part 133, and the control part 134 that were described using FIG. 3.

[Storage Management Device 104]

Figure 12:
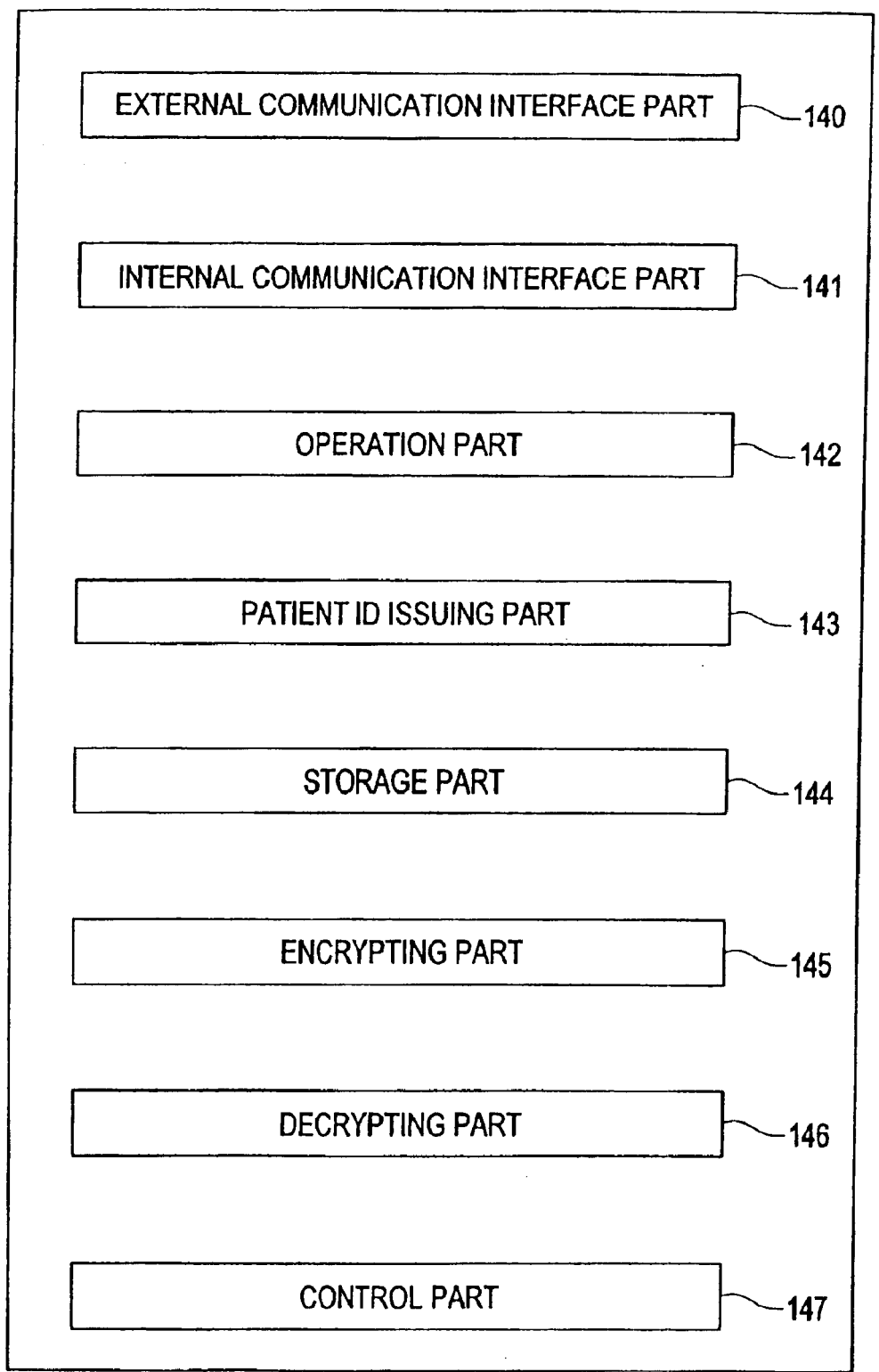
FIG. 12 is a functional block diagram of the storage device 103 shown in FIG. 9.

FIG. 12 is a functional block diagram of the storage management device 104 shown in FIG. 9. As shown in FIG. 12, the storage management device 104 has an external communication interface part 140, an internal communication interface part 141, an operation part 142, a patient ID issuing part 143, a storage part 144, an encrypting part 145, a decrypting part 146, and a control part 147. The external communication interface part 140, the internal communication interface part 141, the operation part 142, the patient ID issuing part 143, the storage part 144, the encrypting part 145, the decrypting part 146, and the control part 147 are basically the same as the external communication interface part 40, the internal communication interface part 41, the operation part 42, the patient ID issuing part 43, the storage part 44, the encrypting part 45, the decrypting part 46, and the control part 47 that were described using FIG. 4.

Hereinafter, an operation of the medical system 101 is described.

First Operation Example

The operation of the medical system 101, from creation of medical image information and diagnostic information in the hospital 10 to storage of patient information in the information storage service agency 11, is the same as the processing described in the first embodiment, using FIGS. 6 and 7.

Second Operation Example

Hereinafter, a description is made of an operation of the medical system in the case where the hospital 110 uses patient information stored in the storage device 8 from the storage management device 4 of the hospital 10 through the first operation example described above. FIG. 13 is a flowchart for explaining the operation example.

Step ST121:

The operation part 142 of the storage management device 104 shown in FIG. 12 is operated by an operator in the hospital 110, patient ID information received from the patient in step ST51 shown in FIG. 10 is inputted, and a patient information use request specifying the patient ID information is created by the control part 147. The patient information use request is sent to the storage device 8 over the leased line 109 from the external communication interface part 140 shown in FIG. 12. The patient information use request is received in the external communication interface part 50 of the storage device 8 shown in FIG. 5.

Step ST122:

By the control part 53 shown in FIG. 5, encrypted patient information is read from the patient information storage part 51 by using the patient ID information specified in the patient information use request received in step ST121 as key.

Step ST123:

The encrypted patient information read in step ST122 is sent to the storage management device 104 over the leased line 109 from the external communication interface part 50 of the storage device 8 shown in FIG. 5. The encrypted patient information is received in the external communication interface part 140 of the storage management device 104 shown in FIG. 12.

Step ST124:

The encrypted patient information received in step ST123 is stored in the storage part 144 of the storage management part 104 shown in FIG. 12.

Step ST125:

A patient operates the operation part 142 of the storage management device 104 shown in FIG. 12 to input a patient password (secret key).

Step ST126:

By the decrypting part 146 of the storage management device 104 shown in FIG. 12, the encrypted patient information stored in step ST124 is decrypted using the patient ID information read from the storage part 144 and the patient password inputted in step ST125.

Step ST127:

The patient information decrypted in step ST126 is sent from the internal communication interface part 141 of the storage management device 104 shown in FIG. 12 to the diagnostic computer 103. The patient information is received in the communication interface part 130 of the diagnostic computer 103 shown in FIG. 11.

Step ST128:

The display part 132 of the diagnostic computer 103 shown in FIG. 11 displays an image reflecting the patient information received in step ST127.

As has been described above, according to the medical system 101, in addition to the effects of the medical system 1, when a patient having been examined in the hospital 10 comes to the hospital 110 for examination, since the hospital 110 can use patient information of the hospital 10, appropriate treatment can be performed using past examination contents of the patient.

Use of patient information of the hospital 10 in the hospital 110 requires patient ID information issued by the hospital 10 and a password known to only the patient. Therefore, only when both the hospital and the patient reach agreement, the hospital 110 can use the patient information. Consequently, the secret of the patient information is properly maintained.

The present invention is not limited to the above described embodiments. For example, although, in the above described embodiments, patient information stored in the storage device 8 includes patient personal information, medical image information, and diagnostic information, patient information of the present invention may include a part of these pieces of information.

Although, in the above described second embodiment, patient information created by the hospital 10 is used in the hospital 110, the present invention can apply to all cases where plural hospitals use patient information created by other hospitals. In the present invention, in the above described second embodiment, when the storage device 8 sends patient information to the storage management device 104, the storage device 8 (information storage service agency 11) may charge the storage management device 104 (hospital 110) for transmission of the patient information.

Many widely different embodiments of the invention may be configured without departing from the spirit and the scope of the present invention. It should be understood that the present invention is not limited to the specific embodiments described in the specification, except as defined in the appended claims.

What is claimed is:

1. A method of managing patient information exchanged between an information use side that creates and uses the patient information, and an information storage side that stores the patient information, the method comprising the steps of:
in the information use side, issuing patient identification information unique to patient and encrypting patient information of the patient;
sending the encrypted patient information from the information use side to the information storage side;
in the information storage side, storing the encrypted patient information received from the information use side in a retrievable format;
in response to a request from the information use side, sending the encrypted patient information pertaining to the request from the information storage side to the information use side;
decrypting, by the information use side, the encrypted patient information by applying the patient identification information and a password decided by the patient; and
in the information use side, using the encrypted patient information received from the information storage side after said decrypting of the encrypted patient information.

2. The patient information management method according to claim 1, wherein the information use side and the information storage side associate and manage the patient identification information of the patient and the patient information.

3. The patient information management method according to claim 2, wherein:
the information use side sends the request to the information storage side together with the patient identification information; and
the information storage side reads the encrypted patient information corresponding to the patient identification information received from the information use side, and sends the read encrypted patient information to the information use side.

4. The patient information management method according to claim 1, wherein the information storage side charges the information use side when the encrypted patient information is sent to the information use side.

5. The patient information management method according to claim 1, wherein:
the information use side stores the patient information for a first period; and
the information storage side stores the encrypted patient information for a second period longer than the first period.

6. A patient information management system comprising:
a storage management device provided in an information use side using patient information; and
a storage device provided in an information storage side storing the patient information, wherein:
the storage management device comprises:
an issuing means for issuing patient identification information unique to a patient;
an encrypting means for encrypting patient information of the patient;
a first sending means for sending the encrypted patient information and a request to use the patient information to the storage device;
a first receiving means for receiving the encrypted patient information from the storage device; and
a decrypting means for decrypting the encrypted patient information by using the patient identification information and a password decided by the patient;

the storage device comprises:
a second receiving means for receiving the encrypted patient information and the request from the storage management device;
a storing means for storing the encrypted patient information;
a control means for reading the encrypted patient information from the storing means in response to the request; and
a second sending means for sending the read encrypted patient information to the storage management device.

7. The patient information management system according to claim 6, wherein the storage management device and the storage device associate and manage the patient identification information of the patient and the patient information.

8. The patient information management system according to claim 7, wherein:
the first sending means of the storage management device sends the request to the storage device together with the patient identification information;
the second receiving means of the storage device receives the patient identification information;
the control means of the storage device reads the encrypted patient information corresponding to the patient identification information received by the second receiving means from the storing means; and
the second sending means of the storage device sends the read encrypted patient information to the storage management device.

9. The patient information management system according to claim 6, wherein the storage device charges the information use side when the patient information is sent to the information use side.

10. The patient information management system according to claim 6, wherein:
the storage management device further has a storing means that stores the patient information for a first period; and
the storing means of the storage device stores the encrypted patient information for a second period longer than the first period.

11. A patient information management system comprising:
a first storage management device provided in a first information use side using patient information;
a storage device provided in an information storage side storing the patient information; and
a second storage management device provided in a second information use side using the patient information, wherein:
the first storage management device comprises:
an issuing means for issuing patient identification information unique to a patient;
an encrypting means for encrypting the patient information of the patient; and
a first sending means for sending the encrypted patient information to the storage device together with the patient identification information;
the second storage management device comprises:
a second sending means for specifying the patient identification information with a request to use the patient information;
a first receiving means for receiving the encrypted patient information from the storage device; and
a decrypting means for decrypting the encrypted patient information received by the first receiving means, wherein said decrypting means decrypts the encrypted patient information by applying the patient identification information and a password decided by the patient; and the storage device comprises:

a second receiving means for receiving the encrypted patient information from the first storage management device and receiving the use request from the second storage management device;

a storing means for storing the received encrypted patient information;

a control means for reading the encrypted patient information from the storing means in response to the use request; and a third sending means for sending the read encrypted patient information to the second storage management device.

12. The patient information management system according to claim 11, wherein the second storage management device uses the patient identification information that the patient obtained from the first storage management device.

13. The patient information management system according to claim 11, wherein the storage device charges the second storage management device when the patient information is sent to the second storage management device.

* * * * *

UNITED STATES PATENT AND TRADEMARK OFFICE
CERTIFICATE OF CORRECTION

PATENT NO. : 6,876,985 B2
DATED : April 5, 2005
INVENTOR(S) : Tatsuo Kawanaka

It is certified that error appears in the above-identified patent and that said Letters Patent is hereby corrected as shown below:

Column 13,
Line 3, after "unique to" insert -- a --.
Line 58, after "for encrypting" insert -- the --.

Signed and Sealed this

Twenty-third Day of August, 2005

JON W. DUDAS
*Director of the United States Patent and Trademark Office*